United States Patent [19]

Suzuki et al.

[11] Patent Number: 5,444,157

[45] Date of Patent: Aug. 22, 1995

[54] CHONDROMODULIN-I PROTEIN

[75] Inventors: Fujio Suzuki, Toyonaka; Yuji Hiraki, Takatsuki; Hideho Tanaka, Machida; Akihito Kamizono, Machida; Jun Kondo, Machida; Yutaka Teranishi, Sagamihara, all of Japan

[73] Assignee: Mitsubishi Kasei Corporation, Tokyo, Japan

[21] Appl. No.: 47,033

[22] Filed: Apr. 13, 1993

Related U.S. Application Data

[63] Continuation of Ser. No. 821,859, Jan. 15, 1992, abandoned, which is a continuation-in-part of Ser. No. 745,497, Aug. 15, 1991, abandoned.

[30] Foreign Application Priority Data

Aug. 23, 1990 [JP] Japan .................................. 2-222178
Feb. 15, 1991 [JP] Japan .................................. 3-022377
Jul. 24, 1991 [JP] Japan .................................. 3-184859

[51] Int. Cl.[6] ............................................ C07K 14/00
[52] U.S. Cl. ..................................... 530/395; 530/350
[58] Field of Search ................... 530/395, 350; 514/8, 514/12

[56] References Cited

FOREIGN PATENT DOCUMENTS 3045265 2/1991 Japan .

OTHER PUBLICATIONS

Neame et al. (Jun. 15, 1990) The Journal of Biological Chemistry, vol. 265 (17). pp. 9628-9632.
Biochemical and Biophysical Research Communications. vol. 175, No. 3, 29 Mar. 1991, Duluth, Minn. US, pp. 971-977, Y. Hiraki et al. "Molecular Cloning of a New Class of Cartilage-Specific Matrix, Chondromodulin-I, Which Stimulates Growth of Cultured Chondrocytes".
Chemical Abstracts, vol. 107, No. 21, 23 Nov. 1987, Columbus, Ohio, US: abstract No. 191734, Y. Hiraki et al. "Combined effects of somatomedin-like growth factors with fibroblast growth factor epidermal growth factor in DNA synthesis in rabbit chondrocytes" p. 155, col. R; & Mol Cell Biochem. vol. 76, No. 2, 1987, The Hague, NL pp. 185-193.
Biological Abstracts.-Microfilms. Abstr. No. 53271 vol. 90, No. 5, 1990, Philadelphia, Pa. US M. Takigawa et al. 'A clonal human chondrosarcoma cell line produces an anti-angiogenic antitumor factor' & Anticancer Res. 10 (2 Part A) 1990, Athens, Greece pp. 311-316.
Journal of Biological Chemistry, vol. 265, No. 17, 15 Jun. 1990, Baltimore US pp. 9628-9633; P. J. Neame et al. 'An 18-kDa Glycoprotein from Bovine Nasal Cartilage'.

*Primary Examiner*—Margaret Parr
*Assistant Examiner*—Lisa Arthur
*Attorney, Agent, or Firm*—Wenderoth, Lind & Ponack

[57] ABSTRACT

A novel chondromodulin-I protein having a molecular weight of about 26,000 dalton on SDS-PAGE and capable of stimulating the growth of chondrocytes with or without FGF and promoting the differential potency of said cells, a DNA encoding said protein, expression vector containing said DNA, a transformant capable of producing recombinant chondromodulin-I protein, a process for producing chondromodulin-I protein by culturing said transformant and a pharmaceutical composition containing chondromodulin-I protein as an active ingredient.

2 Claims, 8 Drawing Sheets

```
Glu Leu Val Arg Lys Ile AAA Thr Thr BBB Thr Thr Arg Arg Leu Arg
 1            5                10                    15

Ser Gly Pro Gln Gly Thr Pro Ala Pro Gly Arg Pro Asn Asn Gly Thr
            20              25                  30

Arg Pro Ser Val Gln Glu Asp Ala Glu Pro Phe Asn Pro Asp Asn Pro
            35              40                  45

Tyr His Gln CCC Glu Gly Glu Ser Met Thr Phe Asp Pro Arg Leu Asp
        50              55              60

His Glu Gly Ile Cys Cys Ile Glu Cys Arg Arg Ser Tyr Thr His Cys
 65              70              75                  80

Gln Lys Ile DDD Glu Pro Leu Gly Gly Tyr His Pro Trp Pro Tyr Asn
            85              90                  95

Tyr Gln Gly Cys Arg Ser Ala Cys Arg Val Ile Met Pro Cys Ser Trp
            100             105                 110

Trp Val Ala Arg Ile Leu Gly Met Val
            115             120
```

Fig. 6

```
Glu Leu Val Arg Lys Ile AAA Thr Thr BBB Thr Thr Arg Arg Leu Arg
  1               5                  10                  15
Ser Gly Pro Gln Gly Thr Pro Ala Pro Gly Arg Pro Asn Asn Gly Thr
             20                  25                  30
Arg Pro Ser Val Gln Glu Asp Ala Glu Pro Phe Asn Pro Asp Asn Pro
         35                  40                  45
Tyr His Gln CCC Glu Gly Glu Ser Met Thr Phe Asp Pro Arg Leu Asp
     50                  55                  60
His Gly Ile Cys Cys Ile Glu Cys Arg Arg Ser Tyr Thr His Cys
 65                  70                  75                  80
Gln Lys Ile DDD Glu Pro Leu Gly Tyr His Pro Trp Pro Tyr Asn
                 85                  90                  95
Tyr Gln Gly Cys Arg Ser Ala Cys Arg Val Ile Met Pro Cys Ser Trp
             100                 105                 110
Trp Val Ala Arg Ile Leu Gly Met Val
                 115             120
```

Fig. 7

```
GAACTGGTAA GAAAAATCCT GACCACA12G ACCACAAGAA GACTACGCAG CGGCCCTCAG    60
GGCACCCCAG CCCCTGGAAG ACCAAACAAC GGAACCAGAC CCAGCGTCCA AGAGGACGCA   120
GAGCCCCTTCA ACCCAGACAA CCCTTACCAC CAG345GAAG GAGAAAGCAT GACATTCGAC  180
CCCAGACTGG ATCATGAAGG AATCTGCTGT ATAGAATGCA GGAGGAGCTA CACCCACTGC   240
CAGAAGATC6 78GAGCCTCT GGGGGGCTAC CACCCATGGC CCTATAACTA CCAGGGCTGC   300
CGTTCCGCCT GCAGAGTCAT CATGCCCCTGT AGCTGGTGGG TGGCCCGCAT CCTGGGCATG  360
GTGTGA                                                              366
```

Fig. 8

```
GAGTTGGTCA GGAAGATAAT GACCACAGAG ACCACAAGAA GACTACGCAG CGGCCCTCAG    60
GGCACCCCAG CCCCTGGAAG ACCAAACAAC GGAACCAGAC CCAGCGTCCA AGAGGACGCA   120
GAGCCCTTCA ACCCAGACAA CCCTTACCAT CAGGAAGGAG AAAGCATGAC ATTCGACCCC   180
AGACTGGATC ATGAAGGCAT CTGCTGTATA GAATGCAGGA GGAGCTACAC CCACTGCCAG   240
AAGATCTGTG AGCCTCTGGG GGGCTACCAC CCATGGCCCT ATAACTACCA              290
```

CHONDROMODULIN-I PROTEIN

This application is a continuation of now abandoned application, Ser. No. 07/821,859 filed on Jan. 15, 1992, which is a continuation-in-part of now abandoned application, Ser. No. 07/745,497 filed Aug. 15, 1991.

BACKGROUND OF THE INVENTION

This invention relates to a novel chondromodulin protein. More particularly, it relates to chondromodulin-I protein capable of stimulating the growth of chondrocytes in the presence or absence of fibroblast growth factor and promoting the differential potency of said cells, an isolated DNA (gene) encoding said protein, expression vectors containing said DNA, transformants capable of producing recombinant chondromodulin-I protein, a process for producing chondromodulin-I protein by culturing said transformants and a pharmaceutical composition containing chondromodulin-I protein as an active ingredient. The present invention also relates to the use of chondromodulin-I protein in the treatment of fracture and various cartilage diseases and as an anti-tumor drug.

Almost all the bones of mammals, except for flat bones such as cranial bone and the like, are formed through a mechanism called "intracartilaginous ossification", which comprises expression of primordial chondrocytes during the embryonic stage, growth and differentiation of said cartilaginous cells, generation of primordial cartilages such as proteoglycan, collagen II, collagen IX, collagen X and the like, infiltration of capillary vessels which is accompanied by the decomposition of ground substance of cartilage and progression of calcification around the vesicles of said ground substance, and the replacement thereof with bone as the final step. Thus, the cartilage metabolism plays a significantly important role in the bone-formation, especially in the elongation of a bone along the axis.

It has been known that a variety of hormones and growth factors participate in the bone-formation (osteogenesis) process, including insulin-like growth factor (IGF1, IGF2), fibroblast growth factor (FGF), growth hormone, tumor cell growth factor (TGF-$\beta$) and the like. It has also been suggested that a certain active factor exists in cartilage, which stimulates the growth and differentiation of chondrocytes. However, there have been no reports which disclose the purification of the factor to such an extent that a single band is obtained on SDS-PAGE, and its definite physiological activity has not been determined. Neam et al. [Peter J. Neam et al., Journal of Biological Chemistry Vol.265, No.17, 9628-9633, (1990)] reported that they separated from bovine cartilage a sugar protein having an amino acid sequence highly similar to that of chondromodulin in the course of their studies for the identification of constitutive proteins in cartilage. However, they still have not elucidated the biological functions of said sugar protein.

The protein which concerns to the above-mentioned growth of chondrocytes and the like is known as chondromodulin protein having biological activities as illustrated below.

The expression of the growth and differentiation of chondrocytes plays an important role in the course of recovery from fracture or various cartilage diseases as follows: inflammatory reaction at the injured site, growth of the periost-derived cells, expression and growth of chondrocytes, synthesis of extra-cellular ground substances, calcification of said substances, and replacement thereof with bone tissues. As can be easily understood, the growth of cartilage tissue at the site of fracture is essential for the formation of bone tissue. Additionally, it is obvious that the growth of the chondrocytes is also important in the course of the recovery from cartilage diseases accompanied by cartilage destruction or injury. Furthermore, before the growth or metastasis of tumor cells, infiltration of blood vessels into tissues occurs for the supply of necessary energy to tumor cells, and therefor the inhibition of such a infiltration is thought to be effective for the prevention of growth or metastasis of tumor cells.

As can be seen from the above, it is desirable to obtain enough amount of chondromodulin protein capable of inhibiting the amplification of chondrocytes or infiltration of blood vessels and thereby providing treating methods effective on the above-mentioned diseases. However, industrial production of said protein from cartilage tissue was extremely difficult and practical application of said protein has been hindered because of the lacking of means to obtain the protein in large amount.

The present inventors have studied extensively with the aim of producing a large amount of chondromodulin protein by the use of recombinant DNA techniques and have now succeeded in the isolation of a novel protein, which belongs to a family of chondromodulin protein, useful for the establishment of the purpose of the invention, cloning of a gene (cDNA) encoding said protein, construction of an expression vector, transformation of heterogeneous cells, and production of recombinant protein by culturing the transformants. The present inventors also investigated physiological activities of thus obtained chondromodulin-I protein and demonstrated that said protein possesses above-mentioned activities and are useful in the treatment of fracture, various cartilage diseases, cancers and the like and can be formulated into pharmaceutical compositions.

SUMMARY OF THE INVENTION

Thus, this invention provides a novel protein chondromodulin-I protein which has a molecular weight of about 26,000 dalton on SDS-polyacrylamide gel electrophoresis and has an ability to stimulate the growth of chondrocytes in the presence or absence of fibroblast growth factor and an ability to promote the differential potency of said cells.

This invention also provides an isolated gene (DNA) encoding chondromodulin-I protein and expression vectors comprising sequences required for the expression of said gene, which comprise, at least, a promoter sequence, signal peptide-like sequence, DNA sequence encoding the chondromodulin-I protein protein, and a terminator sequence, if desired.

This invention further provides a transformant transformed by an expression vector of the invention and a process for producing chondromodulin-I protein by culturing said transformation in an appropriate medium for the expression of the DNA encoding chondromodulin-I protein and recovering the chondromodulin-I protein from the resultant cultured broth.

This invention also provides the recombinant chondromodulin-I protein products produced by the method of present the invention.

This invention also provides the use of chondromodulin-I protein obtained according to the procedure of the invention in the treatment of fracture, various cartilage diseases and cancer.

Purification of the novel chondromodulin-I protein can be conducted by any of conventional procedures known to those skilled in the art. As will be hereinafter described in detail in the Examples, the chondromodulin-I protein was isolated and purified by isolating chondrocytes from cartilage of fetal bovine, culturing the cells, separating the supernatant from cultured broth by centrifugation, concentrating the supernatant by ultrafiltration, subjecting the concentrate to a molecular sieve chromatography on Sephacryl S1200 column, and purifying the resultant product repeatedly with YMC pack C4 chromatography while changing the elution conditions. Thus purified protein of the invention has a molecular weight of about 26,000 dalton on SDS-PAGE and has activities to stimulate the growth of chondrocytes in the presence or absence of fibroblast growth factor (FGF) and to promote the differential potency of chondrocytes.

The amino acid sequence of the purified peptide was determined, which is provided in FIG. 6 (SEQ ID NOS. 1–2). As can be seen from the sequence, the chondromodulin-I protein of the invention is a peptide of 120 or 121 amino acids.

The present inventors then isolated cDNA encoding chondromodulin-I protein, cloned said DNA and constructed expression vectors. A base sequence encoding the chondromodulin-I protein is provided in FIG. 7 (SEQ ID NOS. 3–4).

Once the amino acid and DNA sequences of chondromodulin-I protein are determined, it is easy to obtain active derivatives of chondromodulin-I protein, which falls within the scope of the invention, by conventional methods, such as site specific mutation of DNA, which leads to the deletion, replacement, modification or addition of amino acids without changing the properties of chondromodulin-I protein. Therefore, this invention also provides active recombinant chondromodulin-I protein derivatives obtained by conventional methods. Thus, for the purpose of the invention, as disclosed and claimed herein, the term chondromodulin-I protein refers to both of naturally occurring chondromodulin-I protein and recombinant chondromodulin-I protein produced by the method of the invention.

DESCRIPTION OF THE DRAWINGS

FIG. 6: Amino acid sequence of purified chondromodulin-I protein. In the FIG. 6, AAA is Met or Val; BBB is Glu or Thr; CCC is Gln or deletion; and DDD is Cys or Val.

FIG. 7: Base sequence encoding chondromodulin-I protein. In the FIG. 7, 0 is G or A; 1 is A or G; 2 is C or A; 3 is C or deletion; 4 is A or deletion; 5 is G or deletion; 6 is G or T; 7 is G or T; and 8 is T, G, A or C.

FIG. 8: Base sequence of said PCR fragment (290 bp) encoding parts of amino acid sequence of purified chondromodulin-I protein of FIG. 1 (SEQ ID NO. 7).

DETAILED DESCRIPTION OF THE INVENTION

Figure 1:
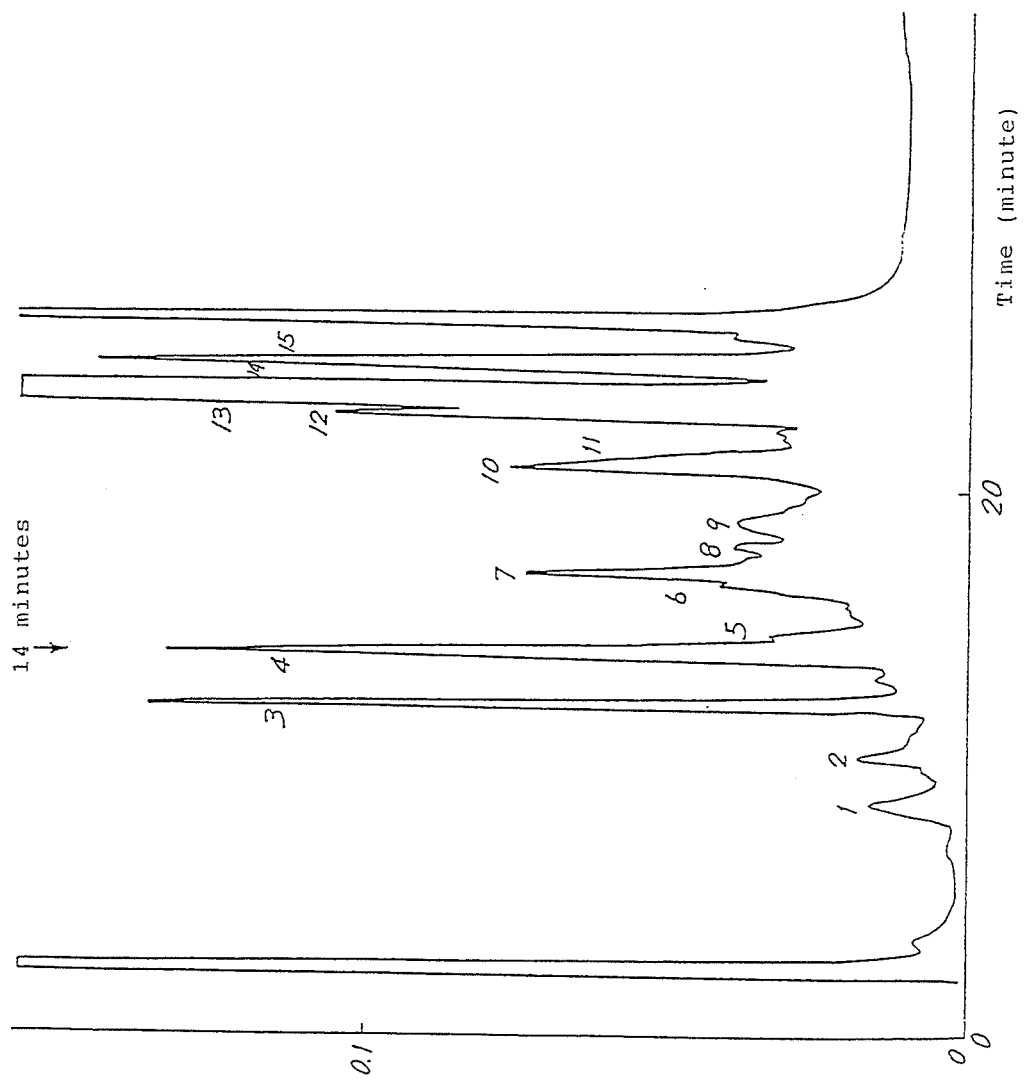
FIG. 1: An elution pattern of chondromodulin-I protein from YMC pack C4 column.

Isolation of cDNA fragment encoding chondromodulin-I protein of the invention can be carried out using any of well known methods. For example, it can be conducted conventionally by preparing cDNA libraries from bovine fetal cartilage using λgt10 phage and transfecting said libraries into $Escherichia$ $coli$ NM 514 cells according to a method disclosed in literatures (see, for instance, Tomizawa et al. "Experiments of Bacteriophage" Iwanami Shoten, 99–174, 1970) and culturing the cells. Positive plaques can be screened by plaque hybridization (The Molecular Cloning, Cold Spring Harbor Laboratory, 320–328, 1982) using a DNA fragment having a base sequence corresponding to part of the previously determined amino acid sequence of purified chondromodulin-I protein to obtain the aimed cDNA encoding chondromodulin-I protein. Probes used in the plaque hybridization can be a partial cDNA prepared by the polymerase chain reaction (hereinafter it is referred to as PCR) (Science, 239,487–491, 1988) using following primers which have base sequences encoding part of amino acid sequence shown in FIG. 6:

+Chain DNA primer corresponding to the amino acid sequence from No. 1 to 7:
 5' GAA/GTTA/GGTA/C/G/TAGA/GAAA/GATA/C/TA/GT 3' (20 nucleotides) (SEQ ID NO. 8); and
 5' GAA/GCTA/C/G/TGTA/C/G/TAGA/GAAA/GATA/C/TA/GT 3' (20 nucleotides) (SEQ ID NO. 9).

−Chain DNA primer corresponding to the amino acid sequence from No. 93 to 98:
 5' TGA/GTAA/GTTA/GTAA/C/G/TGG-CCA 3' (17 nucleotides) (SEQ ID No. 10).

Alternatively, a synthetic oligonucleotide prepared on the basis of DNA sequence deduced from the amino acid sequence of chondromodulin-I protein is also available.

DNA can be prepared from positive plaques after the amplification of phages as described (T. Maniatis et al., Molecular Cloning, Cold Spring Harbor Laboratory, Cold Spring Harbor, N.Y., 85, 1982), digested with an appropriate restriction enzyme such as BamHI or the like, and subcloned into a plasmid such as pUC18, and the base sequence of desired cDNA segment can be determined by, for example, dideoxy method (Sanger et al., Proc. Natl. Acad. Sci. USA, 74: 5463, (1977)). Thus obtained base sequence shown in FIG. 7 is a fragment of 360 or 363 nucleotides long in total and encodes a protein having 120 or 121 amino acids. The sequence comprises base sequences encoding partial amino acid sequences of chondromodulin-I protein presented in FIG. 6 (from No. 1 to 7 and No. 93 to 98). As previously mentioned, the present invention is inclusive of DNA derivatives obtained by conventional methods for the modification as far as said derivatives encodes the active chondromodulin-I protein of the invention.

As the DNA encoding chondromodulin-I protein was cloned and its sequence was determined in the present invention, one can easily construct expression vectors which enable host cells to produce chondromodulin-I protein using the known recombinant technology for example, by inserting into a known expression vector the DNA compound, after modification of 5' terminal or addition of precursor gene at an appropriate site of the vector, downstream from a promoter, using a well known method per se, and introducing the expression vector harboring the cDNA into a host cell such as *Escherichia coli* cell, yeast cell, animal cell or the like according to the method known to one of skill.

This invention can be accomplished using any expression vectors having a promoter at an appropriate site to make the DNA encoding chondromodulin-I protein expressed in a selected host cell. Expression vectors functional in microorganisms such as *Escherichia coli*, *Bacillus subtilis* or the like will preferably comprise promoter, ribosome binding (SD) sequence, chondromodulin-I protein protein-encoding gene, transcription termination factor, and a regulator gene.

Examples of promoters include those derived from *Escherichia coli* or phages such as tryptophane synthetase (trp), lactose operon (lac), λphage $P_L$ and $P_R$, $T_5$ early gene $P_{25}$, $P_{26}$ promoter and the like. These promoter may have modified or designed sequence for each expression vector such as pac promoter (Agr. Biol. Chem., 52: 983–988, 1988).

Although the SD sequence may be derived from *Escherichia coli* or phage, a sequence which has been designed to contain a consensus sequence consisting of more than 4 bases, which is complementary to the sequence at the 3' terminal region of 16S ribosome RNA, may also be used.

The transcription termination factor is not essential. However, it is preferable that an expression vector contains a ρ-independent factor such as lipoprotein terminator, trp operon terminator or the like.

Preferably, these sequences required for the expression of the chondromodulin-I protein gene are located, in an appropriate expression plasmid, in the order of promoter, SD sequence, chondromodulin-I protein gene and transcription termination factor from 5' to 3' direction.

Typical example of expression vectors is commercially available pKK233-2 (Pharmacia). However, a series of plasmids pGEK (Pharmacia), which are provided for the expression of fused proteins, are also employable for the expression of the chondromodulin-I protein gene of the present invention.

A suitable host cell such as *Escherichia coli* can be transformed with an expression vector comprising the DNA encoding chondromodulin-I protein in a conventional manner to give a transformant.

The cultivation of the transformants can be carried out using any of the well known procedures in literatures such as Molecular Cloning, 1982, and the like. The cultivation is preferably conducted at a temperature from about 28° C. to 42° C.

Expression vectors used for transforming other host cells, such as those derived from insects or animals including mammals, consist of substantially the same elements as those described in the above. However, there are certain preferable factors as follows.

When insect cells are used, a commercially available kit, MAXBAC TM is employed according to the teaching of the supplier (MAXBAC TM BACULOVIRUS EXPRESSION SYSTEM MANUAL VERSION 1.4). In this case, it is desirable to make a modification to reduce the distance between the promoter of polyhedrin gene and the initiation codon so as to improve the expression of the gene.

When animal cells are used as hosts, expression vectors preferably contain SV40 early promoter, SV40 late promoter, apolipoprotein E gene promoter, or the like. Specifically, known expression vectors such as pKCR (Proc. Natl. Acad. Sci. USA, 78: 1528 (1981)), pBPV MT1 (Proc. Natl. Acad. Sci. USA, 80:398 (1983)), or the like may be employed after minimum modification, for example, an insertion of cloning site as described in a literature (Nature, 307:604 (1984)), so that the resultant vectors maintain essential functions to serve as expression vectors.

Animal cells usable in the present invention are CHO cell, COS cell, mouse L cell, mouse C127 cell, mouse FM3A cell and the like.

The recombinant polypeptide expressed by the host cells such as microorganisms including *E. coli*, insect cells and animal cells can be recovered from the cultured broth by known methods and identified by, for example, immunoreactions between the expressed protein and a rabbit antiserum raised against a synthetic peptide containing a fragment of chondromodulin-I protein, using a conventional method such as Western blot analysis.

Separation and purification of chondromodulin protein produced by transformants can be conducted using any one of known procedures to one of skill in the art.

Figure 3:
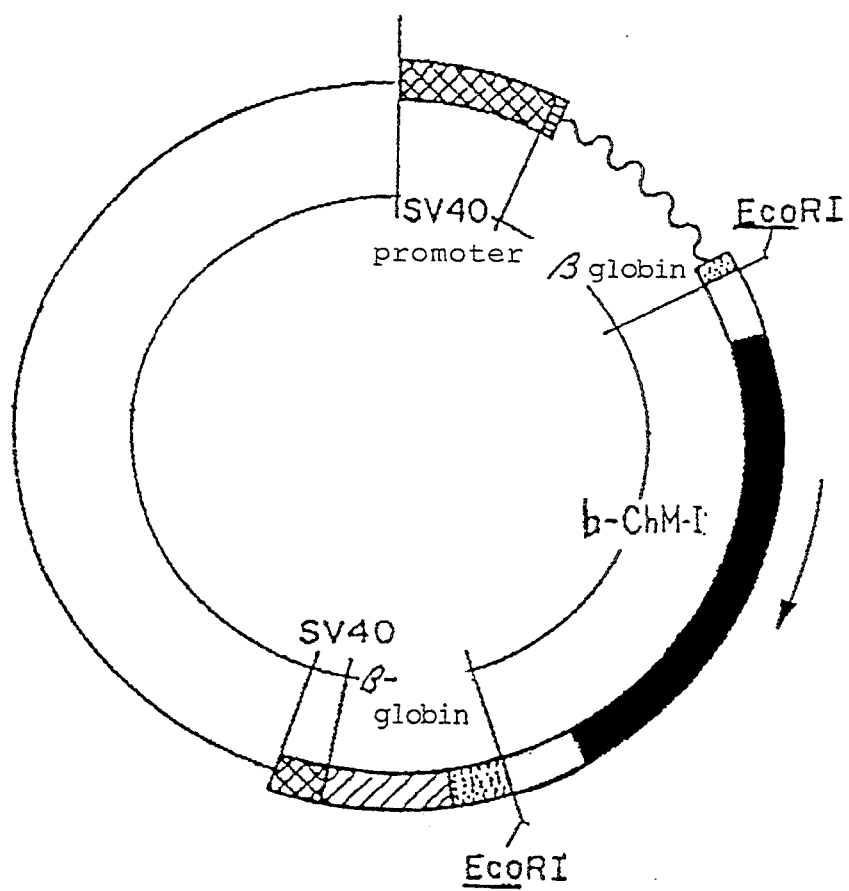
FIG. 3: A schematic illustration for the construction of plasmid pKCRCHM1. Plasmid pKCRCHM3 contains DNA encoding chondromodulin-I protein, which is oriented reversibly.

In the working Examples as mentioned below, illustrative expression plasmids pKCRCHM1 and pKCRCHM3 are constructed and transfected into COS cells according to the known methods in a literature [Ausubel et al., Current Protocols in Molecular Biology, published by Greene Publishing Associates and Wiley-Interscience, Chapter 9.1.1 to 9.1.4 (1987)]. The resultant transformants, when cultivated, expressed products having biological activities of chondromodulin-I protein. The construction protocol of plasmids pKCRCHM1 is shown in FIG. 3. Plasmid pKCRCHM3 contains DNA encoding chondromodulin-I protein reversibly. COS cells transfected with pKCRCHM1 or pKCRCHM3 were grown in ERDF medium containing 10% FCS, and expression of chondromodulin-I protein was analyzed by Western blot analysis.

When proteins in the supernatant of the cultured broth were separated by SDS-PAGE and localized by immunoblotting, a band corresponding to the molecular weight of purified chondromodulin-I protein was found (FIG. 4), which demonstrates that transformants expressed recombinant chondromodulin-I protein.

Biological activities of chondromodulin protein can be determined according to the described method (Suzuki, et al., Methods in Enzymology, 146; 313–320, 1987).

Figure 2:
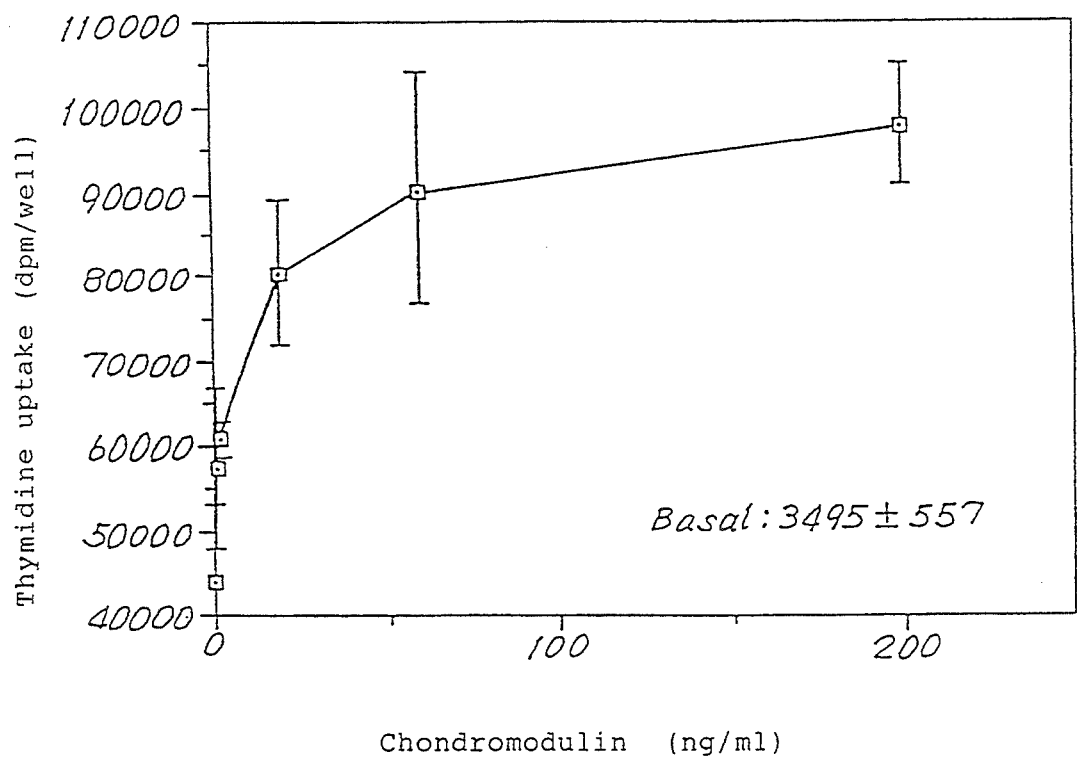
FIG. 2: DNA-synthetic activity of chondromodulin-I protein evaluated on the basis of the uptake of radioactively-labeled thymidine according to the method of Suzuki et al. ( Methods in Enzymology, 146: 313–320, 1987).

Primary cells were isolated from growing costal cartilage obtained from a rabbit and grown in a 96-well plate. When the culture became confluent, [$^3$H]thymidine and 0.6 to 200 ng/ml of chondromodulin-I protein, and 0.4 ng/ml of FGF, if desired, were added to the plate and the uptake of [$^3$H] thymidine was determined. For control experiments, samples lacking chondromodulin-I protein and/or FGF were treated simultaneously. Test results are shown in FIG. 2. FIG. 2 shows that chondromodulin-I protein stimulates the uptake of radioactively-labeled thymidine. Thus, the thymidine uptake in the presence of 200 ng/ml of chondromodulin protein is about 28 times greater than that observed in the absence of chondromodulin protein and FGF, and about 2.2 times greater than that observed in the presence of FGF but absence of chondromodulin protein, which demonstrates that chondromodulin-I protein possesses a potent stimulating effect on the growth of chondrocytes.

The chondromodulin protein-I was also evaluated about the inhibiting activity against vascular infiltration by determining the preventive effect on the growth of vascular endothelial cells. The evaluation was based on the inhibition against [$^3$H]thymidine uptake by aortic endothelial cells as will be hereinafter described in detail in Examples. Thus, when chondromodulin protein was added to bovine aortic endothelial cells, the uptake of radioactive thymidine was apparently inhibited.

As previously stated, chondromodulin protein including chondromodulin-I protein of the invention, its active derivative or a protein product containing chondromodulin-I protein is useful in the treatment of fracture or various cartilage diseases and tumor. When chondromodulin protein or its active derivative is used in clinical treatment, especially in the treatment of fracture or various cartilage disease, it may be applied locally to the site of fracture or cartilage disease by surgical treatment. It can be administered conventionally by injecting intravenously, subcutaneously or directly to the site to be treated after being formulated into an appropriate formulation with a pharmaceutically and physiologically acceptable carrier, excipient or solvent therefor. The preparation of suitable formulations can be carried out using known methods, for example, by mixing with, impregnating into, or applying onto a carrier, solvent, excipient or the like. Examples of physiologically acceptable carriers are bio-adhesives for surgery, including collagen, aterocollagen, gelatin, hyaluronic acid, polyethylene glycol, polylactose, bone cement, hydroxyapatite, ceramics, carbon fiber, fibrin, starch and the like. Any known carriers, solvents, excipients or the like are employable in the preparation of formulations of the invention. The daily dose of chondromodulin protein in the treatment of fractures or cartilage diseases depends on the condition of the subject to be treated. However, it is generally in the range of 1 ng to 10 mg.

When chondromodulin protein, its active derivative or a protein product containing chondromodulin protein is used as an anti-tumor drug, 1 ng to 100 mg of said protein is applied directly to the tumor tissue or injected intravenouly or subcutaneously after formulated into appropriate forms by known methods.

Following Examples further illustrate and detail the invention disclosed, but should not be construed to limit the invention.

EXAMPLE 1

Purification of Chondromodulin Protein and Determination of Partial Amino Acid Sequence 1. Extraction and Purification of Chondromodulin Protein Fetal bovine cartilage (5 kg) was crushed into pieces (several mm in size) and homogenized in 10 times volume per weight of A buffer (1 M guanidine hydrochloride, 0.1M 6-amino-n-caproic acid, 0.02M 2-(N-morpholino)ethanesulfonic acid, pH 6.0) by means of Politron. The homogenate was stirred at 4° C. for 48 hr and centrifuged at 10,000×g for 20 min to separate the supernatant. The supernatant was added with cold acetone gradually to the final concentration of 45% and centrifuged at 4,000 rpm for 30 min to pellet the precipitates. To the supernatant was added cold acetone gradually to the final concentration of 65% and the mixture centrifuged at 4,000 rpm for 30 min to recover precipitates in fractions of acetone concentration of 45 to 65%. The pellet was dissolved in 6 L of B buffer (4M guanidine hydrochloride, 0.1M 6-amino-n-caproic acid, 1M NaCl, 0.02M Tris-HCl, pH 8.0) at 4° C. and centrifuged at 10,000 rpm for 30 min to remove insoluble materials as a pellet. The supernatant was concentrated to the final volume of 500 ml by a successive ultrafiltration using Amicon ultrafilter XM300, Amicon ultrafilter XM50, and Amicon ultrafilter YM10. A portion of the concentrate (30 ml) was then subjected to molecular sieve chromatography using Sephacryl S200 column (2.6 cm diameter and 100 cm long) eluting with B buffer. Fractions eluted from 230 ml to 310 ml were pooled and dialyzed against distilled water at 4° C. for 2 days. The dialyzate was chromatographed on Heparin-Toyopearl column equilibrated with C buffer (0.15M NaCl, 0.03% CHAPS (surfactant), 0.025M sodium phosphate, pH 7.4). After washing the column thoroughly with C buffer, it was eluted with C buffer containing 0.5M NaCl, and then with C buffer containing 1.2M NaCl. The fraction eluted with the solvent containing 1.2M NaCl was chromatographed on YMC-pack C4 column (AP-802 S-5 300A C4, 0.46×15 cm) equilibrated with 0% acetonitrile/isopropylalcohol (3/7 v/v) containing 0.1% TFA (trifluoroacetic acid). Elution was effected by a linear gradient of the same solvent containing 20% to 70% of organic solvent. Active peaks were pooled and each peak was analyzed fluorometrically (excitation: 280 nm; maximal absorption: 345 nm). The elution pattern is given in FIG. 1. Fraction eluted at 14 min was dried under vacuum, dissolved in 60 μl of 50% TFA, applied to a glass filter treated with polybrene and subjected to the Edman degradation for the determination of amino acid sequence using 470A Sequencer (Applied Biosystems, Inc.). Phenylthiohydantoin (PTH) amino acid was identified using MCIgel ODS 1Hu column (0.46×15 cm) employing a single solvent elution with acetate buffer (10 mM acetate buffer, pH 4.7, 0.01% SDS, 38% acetonitrile) (flow rate: 1.2 ml/min; temperature: 43° C.; detection of PTH amino acid: absorbance at 269 nm). Peptide fragments were obtained by dissolving the purified protein in 50 mM Tris-HCl buffer, pH 9.0, containing 5M urea, treating with lysilendopeptidase (Wako Junyaku, Japan) (enzyme:substrate=1:200) at 37° C. for 6 hr, and subjecting to the Edman degradation using the Sequencer in a similar manner as above. As a result, the amino acid sequence of the aimed protein was identified as shown below.

N terminus:

Glu—Leu—Val—Arg—Lys—Ile—Val/Met—Thr—Xaa—Glu—Thr—Thr—Arg—Arg—

Leu—Arg—Ser—Gly—Pro—Gln—Gly—Gly—Pro—Ala—Pro—Gly—Arg—Pro (SEQ ID NO. 11)

wherein Xaa represents the amino acid not identified.

Lysilendopeptidase fragment:

Ile—Val—Glu—Pro—Leu—Gly—Gly—Tyr—Asp—Pro—Trp—Pro—Tyr—Asn—Tyr—

Gln—Gly—Ser—Arg—Ser—Ala. (SEQ ID NO. 12)

The purified chondromodulin protein, when applied to 12.5% SDS-polyacrylamide gel electrophoresis, gave a band corresponding to a molecular weight of about 26,000 dalton.

EXAMPLE 2

Evaluation of Activities of Chondromodulin Protein

Isolation and cultivation of cells used in the experiments and the evaluation of activities were carried out substantially in accordance with the described method (Suzuki, et al., Methods in Enzymology, 146: 313–320, 1987). Cells were isolated from growing costal cartilage excised from a young New Zealand strain rabbit (400–600 g in weight) and suspended into a 1:1 mixture (hereinafter, referred to as FAD medium) of Ham's F-12 medium and Durbecco's modified medium containing 10% fetal bovine serum (FCS) at a cell density of $10^5$ cells/ml. The cell suspension (0.1 ml) was dispersed into 96-well plate, which had been coated with type I collagen (50 µg/ml)overnight and washed with FAD medium, and incubated at 37° C. under atmosphere of 5% $CO_2$ with changing the medium every other day.

The DNA-synthetic activity was evaluated as follows. Cells were grown in the above 96-well plate until the culture became confluent, then the cells were grown in FAD medium containing 0.3% FCS for 24 hr. The culture was incubated for 22 hr in 0.1 ml of FAD medium containing 0.06 to 20 ng of chondromodulin protein, 0.04 ng of FGF (fibroblast growth factor) and 0.3% FCS. The cultivation was continued another 4 hr after the addition of 10 µl of [$^3$H]thymidine (130 µCi/ml) and cells were washed three times with ice-cold phosphate-buffered saline (20 mM phosphate buffer, pH7.0, 0.15M sodium chloride), extracted with 5% trichloroacetic acid and then with ethanol/ether (3:1 in volume). After the extraction, the precipitate left was dissolved in 0.3M sodium hydroxide, neutralized with 1/20 volume of 6N HCl and the radioactivity was detected by means of a scintilation counter. Results are given in FIG. 2. FIG. 2 shows that the uptake of radioactive thymidine in the presence of 200 ng/ml of chondromodulin protein was apparently increased and it was about 28 folds of that observed in the absence of FGF and about 2.2 folds of that observed in the presence of 0.4 ng of FGF, demonstrating that the chondromodulin protein possesses a potent stimulating effect on the growth of chondrocytes.

EXAMPLE 3

Inhibition Activity of Chondromodulin Protein Against the Growth of Vascular Endothelial Cells The inhibition activity of chondromodulin protein against the growth of vascular endothelial cells was evaluated using bovine aortic endothelial cells. Thus, bovine aortic endothelial cells were inoculated into α-MEM medium containing 0.1 ml of 20% FCS in a 96-well plate at a cell density of $2 \times 10^3$ cells/well and grown in a $CO_2$ incubator at 37° C. for 48 hr, when the medium was replaced by a freshly prepared one and 0 to 3 µg/ml of chondromodulin protein added thereto. After 12-hour incubation at 37° C., [$^3$H]thymidine was added to each well (1 µCi/well) and the plate was allowed to stand for 4 hr at 37° C. After the completion of the uptake of radioactively-labeled thymidine, cells were harvested using cell harvester and radioactivity detected on LKB plate. Results are given in Table 1 below. Table 1 shows that chondromodulin protein inhibits the growth of vascular endothelial cells effectively.

TABLE 1

| chondromodulin protein (µg/ml) | 3 | 1 | 0.45 | 0.15 | 0.068 | 0.023 | 0.001 |
|---|---|---|---|---|---|---|---|
| [$^3$H]thymidine uptake (%)* | 24.2 | 36.4 | 40.4 | 74.6 | 59.2 | 71.6 | 60.1 |

*% to control

EXAMPLE 4

Preparation of cDNA Fragments of Chondromodulin Protein by PCR

1. Extraction of mRNA

Fetal bovine cartilage cDNA which serves as the substrate was prepared conventionally. In brief, poly (A) RNA was obtained from 10 g of bovine growth cartilage according to 8M guanidine-HCl method (Proc. Natl. Acad. Sci. USA, 74: 3399–3403, 1977). Ten µg of fetal bovine growth cartilage was crushed in 60 ml of a solution containing 8M guanidine HCl, 10 mM sodium acetate, pH 5.5, 0.5 mM DTT (dithiothreitol), and the mixture was centrifuged. The supernatant was mixed with 50% volume of ethanol and allowed to stand for 30 min at −20° C. to precipitate total RNA. The fraction containing RNA was recovered by centrifugation and dissolved into 30 ml of a solution containing 7M guanidine-HCl, 10 mM sodium acetate, pH 5.5, 20 mM EDTA and 1 mM DTT. The solution was mixed with 50% volume of ethanol, and the mixture was allowed to stand for 30 min at −20° C. and centrifuged to recover precipitated RNA. The above procedure was repeated once more and RNA so obtained was dissolved in 12.5 ml of 20 mM EDTA and extracted with butanol/chloroform (1:4). To the aqueous layer was added 37.5 ml of 4M sodium acetate, pH 5.5, and the mixture was allowed to stand overnight at −15° C. and centrifuged to yield RNA. After repeating the above procedures three times, there was obtained 6 mg of RNA, which was dissolved in 2.25 ml of a solution of 20 mM tris-HCl (pH 7.5) and 1 mM EDTA, incubated at 65° C. for 5 min and quenched rapidly by pouring into ice-cold water.

The mixture was combined with 0.25 ml of 5M NaCl and subjected to a chromatography using oligo(dT)cellulose column (P-L Biochemical, Inc., column volume: 0.5 ml). Adsorbed mRNA was eluted with autoclaved distilled water to yield 104 μg of poly (A) RNA (mRNA).

2. Preparation of cDNA

Synthesis of cDNA was conducted by cDNA Synthetic System plus (Amersham, Inc.). To a mixture of 10 μl of poly (A) RNA (10 μg), 10 μl of a reaction buffer for the synthesis of the first strand, 2.5 μl of sodium pyrophosphate solution, 2.5 μl of human placental ribonuclease inhibitor, 5 μl of a mixture containing deoxyribonucleotide triphosphates and 2.5 μl of oligo (dT) primer was added 2.5 μl of sterilized distilled water to a final volume of 45 μl. After stirring gently, the mixture was combined with 5 μl of a reverse transcriptase (100 units), mixed, incubated at 42° C. for 45 min and placed on an ice-bath.

The resultant mixture was then combined with 93.5 μl of a reaction buffer for the synthesis of second strand, 5 μl of E. coli ribonuclease H, 32.8 μl of E. coli DNA polymerase I and 43.7 μl of sterilized distilled water were added to the final volume of 225 μl. Incubation was conducted at 12° C. for 60 min, at 22° C. for 60 min and at 70° C. for 10 min. After the addition of 2.5 μl of T4 polymerase (10 units), the incubation was continued another 10 min at 37° C. and the resultant double stranded DNA was recovered by ethanol precipitation (yield, 2 μg), which was dissolved in 200 μl of sterilized distilled water.

3. Polymerase Chain Reaction

A solution of 2 μl (20 ng) of cDNA in sterilized distilled water was used as substrate. PCR was carried out by Perkin Elmer Cetus DNA Thermal Cycler using Gene Amp DNA Amplification Reagent Kit (Takara Syuzo, Japan) according to the manufacture's instruction. Oligonucleotide primers for PCR were designed on the basis of amino acid sequence of chondromodulin-I protein as shown in the Sequence FIG. 6 as follows.
Primer #1:
+chain DNA primer corresponding to the amino acid sequence from No. 1 to 7:
5' GAA/GTTA/GGTA/C/G/TAGA/GAAA/GATA/C/TA/GT 3' (20 nucleotides);
primer #2:
5' GAA/GCTA/C/G/TGTA/C/G/TAGA/GAAA/GATA/C/TA/GT 3' (20nucleotides); and
primer #3:
−chain DNA primer corresponding to the amino acid sequence from No. 93 to 98:
5' TGA/GTAA/GTTA/GTAA/C/G/TGGC/CA 3' (17 nucleotides).

The reaction mixture contained 2 μl (20 ng) of substrate cDNA, 10 μl of ×10 reaction buffer (500 mM potassium chloride, 100 mM Tris-HCl (pH 8.3), 15 mM magnesium chloride, 0.1 w/v % gelatin), 16 μl of 1.25 mM 4dNTPs, 5.5 μl each of 40 μM primer 1, primer 2 and primer 3 and 0.5 μl of Taq DNA polymerase in a total volume of 100 μl. PCR was conducted by repeating 35 times of reaction cycle, which comprises the following steps: pre-treatment at 94° C. for 10 min, denaturation at 94° C. for 1 min, annealing at 44° C. for 1.5 min and elongation at 72° C. for 2 min. After the completion of the 35 times of the reaction cycle, the resultant mixture was extracted with phenol/chloroform (1:1) and precipitated with ethanol. The precipitates was dissolved in 20 μl of sterilized distilled water and electrophoresed on 5% acrylamide gel. DNA was isolated conventionally by cutting a DNA band corresponding to 290 bp from the gel and precipitating with ethanol and dissolved into 16 μl of sterilized distilled water. To the solution was added 2 μl of ×10 T4 DNA polymerase buffer (0.33M tris-HCl (pH 7.9), 0.66M potassium acetate, 0.1M magnesium acetate, 5 mM DTT), 1 μl of 1.25 mM 4dNTPs, 1 μl (6 units) of T4 DNA polymerase to obtain a reaction mixture of a total volume of 20 μl. The mixture, when incubated at 37° C. for 30 min, gave a double stranded DNA fragment (blunt end), which was then inserted into SmaI site of pUC18 vector and subjected to the determination of base sequence by Fluorescent DNA Sequencer (Genesis 2000; Dupont). The base sequence of said PCR fragment (290 bp) is shown in the Sequence FIG. 8. The 290 bp DNA fragment encodes parts of amino acid sequence obtained from the purified chondromodulin-I protein as shown in the Sequence FIG. 6. Thus, in the amino acid sequence which coded by said base sequence, the sequence from N-terminal to the 28 amino acid is identical with 1 to 28 amino acid sequence of purified chondromodulin-I protein, and the sequence from C-terminal to proceeding 15 amino acids is identical with 83 to 95 amino acid sequence of purified chondromodulin-I protein, respectively.

EXAMPLE 5

Screening of a Full Length cDNA of Bovine Chondromodulin Protein

A cDNA library was constructed by packaging the fetal bovine cartilage cDNA prepared in Example 1 into λgt10 phage using cDNA cloning system (Amersham Inc.). Thus, to a solution of 2 μg of double stranded cDNA in 13.5 μl of distilled water was added 2 μl of L/K buffer, 2.5 μl of EcoRI adapter and 2 μl of T4 DNA ligase (5 units). After mixing thoroughly, the mixture was incubated overnight at 15° C. The ligation mixture was applied to a column attached to the kit, which was previously equilibrated with TE buffer (10 mM tris-HCl, pH 7.4, 1 mM EDTA), to separate cDNA to which the adapter ligated properly. Resultant 770 μl of cDNA solution was mixed with 86 μl of L/K buffer and 10 μl of T4 kinase (80 units), and the mixture incubated at 37° C. for 30 min, followed by extractions by phenol/chloroform (1:1) (×2) and chloroform/isoamyl alcohol (24:1) (×2) and concentration with butanol to 220 μl. DNA was recovered by subjecting the concentrate to ethanol precipitation by the addition of 20 μl of 4M sodium acetate (pH 5.5) and 500 μl of ethanol, and dissolved in 40 μl of distilled water. To 4 μl of DNA solution was added 2 μl of λgt10 arm, 1 μl of L/K buffer, 2 μl of distilled water and 1 μl of ligase, and incubated overnight at 15° C. The cDNA to which adapter ligated was packaged into λphage particles by means of Stratagene's Gigapack Gold Packaging Kit according to the manufacture's instruction using 4 μl (80 ng) of cDNA solution. Phage stock was prepared by mixing the reaction mixture with 50 μl of phage-diluting solution (100 mM NaCl, 8 mM magnesium chloride, 50 mM Tris HCl, pH 7.5, 0.01% gelatin) and 20 μl of chloroform. Titer of the resultant DNA bank was $2.4 \times 10^6$ plaque forming units (PFU)/ml when tested on E. coli strain NM 514, and $2 \times 10^{11}$ PFU/ml on the same strain after amplification. The amplified DNA bank was used as the cDNA library for the screening of chondromodulin protein cDNA as described below.

Screening was conducted according to the manual attached to the Cloning System using a 15 cm plate. Approximately $5.4 \times 10^5$ clones of phage were transfected into E. coli strain NM514 and grown in 27 Petri dishes (plate of 15 cm diameter) each containing LB soft-agar medium (1% yeast extract, 0.5% bacto-trypton, 0.5% sodium chloride, 0.7% agarose, sterilized by autoclave) at a concentration of $2.0 \times 104$ clone/plate at 37° C. for 7.5 hr. The plaque hybridization was carried out by transferring λphage clones to nitrocellulose filter (BA85, S & S Inc.). Thus, phage particles from one plate were transferred to two nitrocellulose filters, and each filter was placed for 2 min on a filter paper previously treated with 0.1M sodium hydroxide and 1.5M sodium chloride, and then for 5 min on a filter paper previously treated with 1.5M sodium chloride and 0.5M Tris-HCl, pH 7.4. Thereafter, filters were washed with 2×SSC, air-dried on dry filter papers and allowed to stand for 2 hr at 80° C. After washing with 2×SSC, each filter was immersed in 1.5 ml of hybridization buffer [6×SSC, 0.1% SDS, 5×Denhardt's reagent (50×Denhardt, 1% FCA, 1% polyvinylpyrrolidone, 1% Ficol 400), 10 μg/ml denatured salmon sperm DNA] at 62° C. for 2 hr. The 290 bp DNA fragment obtained in Example 4 was labeled with 32p using Random Primer DNA Labeling Kit (Amersham, Inc.) according to the manufacture's instruction. Hybridization was performed by incubating the filters in a hybridization buffer containing 32P-labeled DNA (1 μCi/ml) at 62° C. for 20 hr. After hybridization, the filters were washed in 6×SSC and 0.1% SDS at room temperature for 15 min and twice in 2×SSC and 0.1% SDS at 62° C. for 30 min and detected by autoradiography.

There were about 1,300 plaques which gave positive signals at corresponding positions on both of paired filters. Single plaque hybridization was conducted by plaque hybridization in a similar manner as above to give 10 positive phages. Phages were recovered by punching the plaques with a glass capillary pipet and suspending it into 500 μl of SMG buffer (50 mM Tris-HCl, pH 7.5, 100 mM sodium chloride, 10 mM magnesium chloride, 0.01% gelatin), and stored under cool in the presence of 10 μl of chloroform.

EXAMPLE 6

Subcloning of cDNA Fragment and Sequence Analysis thereof

DNA fragments were extracted from λphage clones and subcloned into plasmids pUC18 and pUC 19. A suspension of about $2 \times 105$ λphage clones in SMG buffer were infected into $3 \times 10^7$ E- coli strain NM514 at 37° C. for 15 min and cells were grown in LB plate (15 cm in diameter) at 37° C. for 8 hr in the same manner as described in Example 2. The plate was allowed to stand for 1 hr at 4° C. and shaken with 8 ml of SMG buffer at 4° C. for 2.5 hr. To the resultant lysate was added 2 drops of chloroform with stirring and centrifuged at 2,000 rpm for 10 min to separate supernatant.

The supernatant was treated with 1 μl/ml of bovine pancreatic DNase I at room temperature for 30 min to digest E. coli genome. The mixture was placed on an ice-bath over a period of 30 min after the addition of 1M NaCl, and then centrifuged at 9,300 rpm for 10 min. To the 3 ml of supernatant was added 3 g of polyethyleneglycol 8000 and the solution placed on an ice-bath for 1 hr and centrifuged at 9,300 rpm for 10 min to separate phage particles. Phages were suspended in 3 ml of SMG buffer, mixed with an equal volume of chloroform, stirred and centrifuged at 2,200 rpm for 15 min. After dissolving 2.25 g of cesium chloride into the supernatant, the mixture was centrifuged at 38,000 rpm at 15° C. for 19 hr by Hitachi SW55Ti Rotar (Hitachi, Japan) and a band containing phage particles was removed from a side of the tube using a injector fitted with 21 G needle. Thus obtained phage suspension was dialyzed against 1 L of a solution of 10 mM sodium chloride, 50 mM Tris-HCl, pH8.0 and 10 mM magnesium chloride twice over a period of 1 hr for each trial. Phage protein was digested by mixing the dialyzate with 20 mM EDTA, 50 μg/ml of proteinase K and 0.5% SDS and allowing to stand for 1 hr at 56° C. After the digestion, the mixture was extracted with an equal volume of phenol (×1), an equal volume of phenol/chloroform (1:1) (×1) and an equal volume of chloroform (×1), successively and centrifuged at 15,000 rpm for 1 min to separate the aqueous layer. The aqueous solution was then subjected to ethanol precipitation to obtain phage DNA, which was dissolved in 25 μl of sterilized distilled water and 1.5 μl of the DNA solution was subjected to the sequence analysis. DNA was digested with restriction enzyme BamHI and the digestion mixture was electrophoresed on agarose gel to determine the size of inserted cDNA fragment. DNA (20 μl ) from a clone containing the longest insertion was digested with BamHI and the resultant cDNA fragment (insertion) was cloned into BamHI site of a cloning vector pUC 18 to obtain plasmid pUCHM26. Cloned DNA was digested with BamHI/BglII and two cDNA fragments of about 0.5 kb and about 0.9 kb were isolated, cloned into BamHI site of pUC18 and subjected to sequence analysis using Fluorecent DNA Sequencer (Dupont). The resulting cDNAs consist of 363 and 360 base pairs encoding 121 and 120 amino acids, respectively. Each amino acid sequence includes N-terminal amino acids of chondromodulin protein. The base sequence of the cDNA is shown in the Sequence FIG. 7.

EXAMPLE 7

Construction of Expressing Plasmid Encoding Chondromodulin-I Protein

Plasmid pUCHM26 containing chondromodulin protein cDNA obtained in Example 6 was constructed substantially in accordance with the description of a literature (Molecular Cloning, Cold Spring Harbor Laboratory, p.86–96, 1982). Ten μg of the plasmid DNA was digested with restriction enzyme ScaI. The digestion mixture was extracted with phenol/chloroform and subjected to ethanol precipitation to obtain DNA fragment and dissolved into 10 μl of water.

Plasmid pUCHM261 was constructed by ligating EcoRI linker comprising 8 bases (5' GGAATTCC 3') at the ScaI site of the ScaI digested DNA according to the known method Maniatis et al., Molecular Cloning, Cold Spring Harbor Laboratory, p.396, 1982). Ten μg of plasmid pUCHM261 DNA was digested with restriction enzyme EcoRI. About 1.25 kb DNA fragment encoding chondromodulin protein precursor was purified by subjecting the digestion mixture to electrophoresis on 0.8% agarose gel to separate said fragment from other fragments and purifying form the gel according to the known method (Molecular Cloning, Cold Spring Harbor Laboratory, p.164, 1982). On the other hand, 0.05 μg of expression vector pCDL-SRα296 DNA was digested with restriction enzyme EcoRI and DNA was isolated by extracting the digestion mixture with phenol/chloroform followed by ethanol precipitation. The resultant DNA was dephosphorylated with bacterial alkaliphosphatase, purified by phenol/chloroform extraction and ethanol precipitation, and dissolved in 10 μl of water. Thus prepared 0.01 μg of pCDL-SRα296 vector and 0.1 μg of EcoRI fragment of chondromodulin-I cDNA were ligated by the use of DNA ligation kit (Takara Syuzo 6021). The ligation mixture was used to transform E. coli HB 101 and the transformants were analyzed about the presence of plasmids containing chondromodulin protein cDNA and detected pKCRCHM1 and pKCRCHM3 which encode bovine chondromodulin-I gene (depicted as b-ChM-I in FIG. 3) oriented forward and reverse, respectively.

The construction protocol of plasmids pKCRCHM1 and pKCRCHM3 are given in FIG. 3.

EXAMPLE 8

Production and Purification of Recombinant Chondromodulin-I Protein

1. Transfection of COS cells, Expression of Chondromodulin Protein and Isolation Thereof COS cells were transfected with the expression plasmids pKCRCHM1 or pKCRCHM3 constructed in Example 7 according to the known method [Ausubel, et al., Current Protocols in Molecular Biology, Greene Publishing Associates and Wiley-Interscience, Chapter 9.1.1 to 9.1.4 (1987)]. Thus, COS cells were grown in ERDF medium (Kyokuto Seiyaku, Inc., Japan) containing 10% FCS in a Petri dish (9 cm in diameter) until the culture became semi-confluent. At this point, medium was removed from the plate and previously prepared DNA solution was added dropwise thereto and the plate allowed to stand for 30 min at room temperature. The DNA solution was prepared, for each 9 cm-Petri dish, by mixing 300 μl of 2×HEBS solution [1.6% sodium chloride, 0.074% potassium chloride, 0.05% disodium hydrogen phosphate 12 hydrates, 0.2% dextrose, 1% HEPES (pH 7.0)], 10 μg of plasmid DNA and 500 μl of sterilized water in a total volume of 570 μl in an Eppendorph centrifuge tube. To the DNA solution was added dropwise 30 μl of 5M calcium chloride solution while stirring vigorously in a vortex mixer for several min. The tube was allowed to stand for 30 min at room temperature in the vortex mixer with stirring intermittently at intervals of about 10 min to obtain a DNA solution.

After the addition of DNA solution to COS cells in 9 cm-plate as mentioned above, the plate was allowed to stand for 30 min at room temperature. To the plate was added 9 ml of ERDF medium containing 10% FCS, and the plate was incubated at 37° C. for 4 to 5 hr under an atmosphere of 5% $CO_2$. After the removal of medium from the plate, cells were washed by adding 5 ml of 1×TBS++ solution (25 mM Tris-HCl, pH 7.5, 140 mM sodium chloride, 5 mM potassium chloride, 0.6 mM disodium hydrogen phosphate, 0.08 mM calcium chloride, 0.08 mM magnesium chloride) and then discarding said solution. To the cells in the plate was added 5 ml of 1×TBS++ containing 20% glycerol and allowed to stand for 1 to 2 min at room temperature followed by the removal of supernatant. After washing cells with 5 ml of 1×TBS++, 10 ml of ERDF medium containing 10% FCS was added to the plate and the plate was incubated at 37° C in the presence of 5% $CO_2$ for 48 hr.

The cultured broth was recovered, centrifuged at 1,500 rpm for 2 min and the supernatant was chromatographed on Heparin-Toyopearl column previously equilibrated with C buffer (0.15M NaCl, 0.03% CHAPS (surfactant), 0.025M sodium phosphate, pH 7.4). The column was washed with C buffer thoroughly and eluted with C buffer containing 0.5M NaCl, then with C buffer containing 1.2M NaCl. The 1.2M NaCl fraction was concentrated with Centricon-10 (Amicon) to obtain a protein sample.

2. Analysis and Assay

Figure 4:
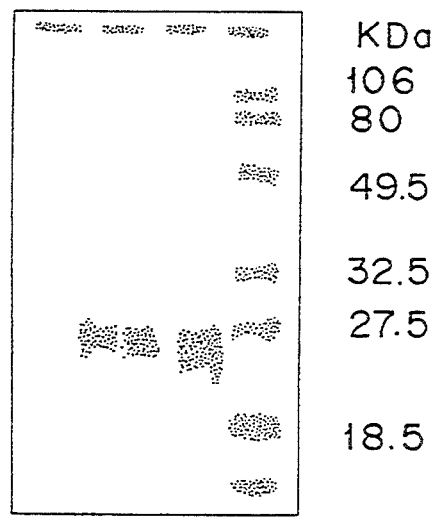
FIG. 4: Western blot analysis for the detection of chondromodulin-I protein contained in the supernatant of a cultured broth of COS cells transformed with an expression vector of the invention.

The expression of chondromodulin protein by transformants were confirmed by SDS-PAGE and Western Blot as follows. Ten μg of protein sample obtained in above 1 (corresponding to 1 ml of a cultured broth) was loaded on 0.1% SDS—12.5% polyacrylamide gel (70×85×1 mm) employing as size marker a commercially available PRESTAINED SDS-PAGE STANDARDS (for low-molecular-weight molecules) (Biorad). Electrophoresis was carried out at a constant current of 30 mA for 45 min in Tris buffer (25 mM Tris-HCl, pH 8.3, 192 mM glycine, 0.1% SDS) as electrode buffer. Thereafter, DNA was transferred electrophoretically to a nitrocellulose filter by superposing the gel onto a filter BA-85 (manufactured by S & S, pore size: 0.45 μm), impressing a constant current of 145 mA for 45 min between the gel (cathode) and the filter (anode). The filter was then immersed into TBST buffer (20 mM Tris-HCl, pH 8.0, 150 mM NaCl, 0.05% Tween 20) containing 5% (w/v) skim milk for 1 hr, followed by washing with TNT buffer (20 mM Tris-HCl, pH7.4, 2 mM EDTA, 0.14M NaCl, 0.05% Tween 20) (×2), briefly. The filter was treated with rabbit anti-peptide antibody (antibody raised against a synthetic peptide containing amino acid sequence corresponding to amino acid 8 (Thr) to 34 (Pro) of matured chondromodulin protein plus an additional amino acid Cys at the C-terminus) in 10 ml of TBST buffer at 4° C. overnight. After 15-minute washing with TNT buffer (×3), the filter was reacted with horseradish peroxidase conjugated goat anti-rabbit antibody (Biorad) at 37° C. for 1 hr, washed with TNT buffer for 15 min (×4), and then with distilled water briefly, and visualized with 50 ml of peroxidase-color-producing reagent (40 ml water, 30 mg 4-chloro-1-naphtol, 10 ml methanol, 20 μl aqueous hydrogen peroxide). Results are shown in FIG. 4. Lane 1: total protein contained in the supernatant obtained from the cultured broth of COS7 cells transformed with pKCRCHM3; lane 2: total protein contained in the supernatant obtained from the cultured broth of COS7 cells transformed with pKCRCHM1; lane 3: purified chondromodulin protein; lane 4: protein used as a molecular size marker.

As can be seen from FIG. 4, the migration pattern of protein fractions obtained from each cultured broth of COS7 cells transformed with plasmid pKCRCHM3 or pKCRCHM1 are consistent with that of purified chondromodulin protein. Thus, the recombinant chondromodulin protein was identified as the purified chondromodulin protein.

EXAMPLE 9

Evaluation of Activities of Recombinant Chondromodulin-I Protein

Figure 5:
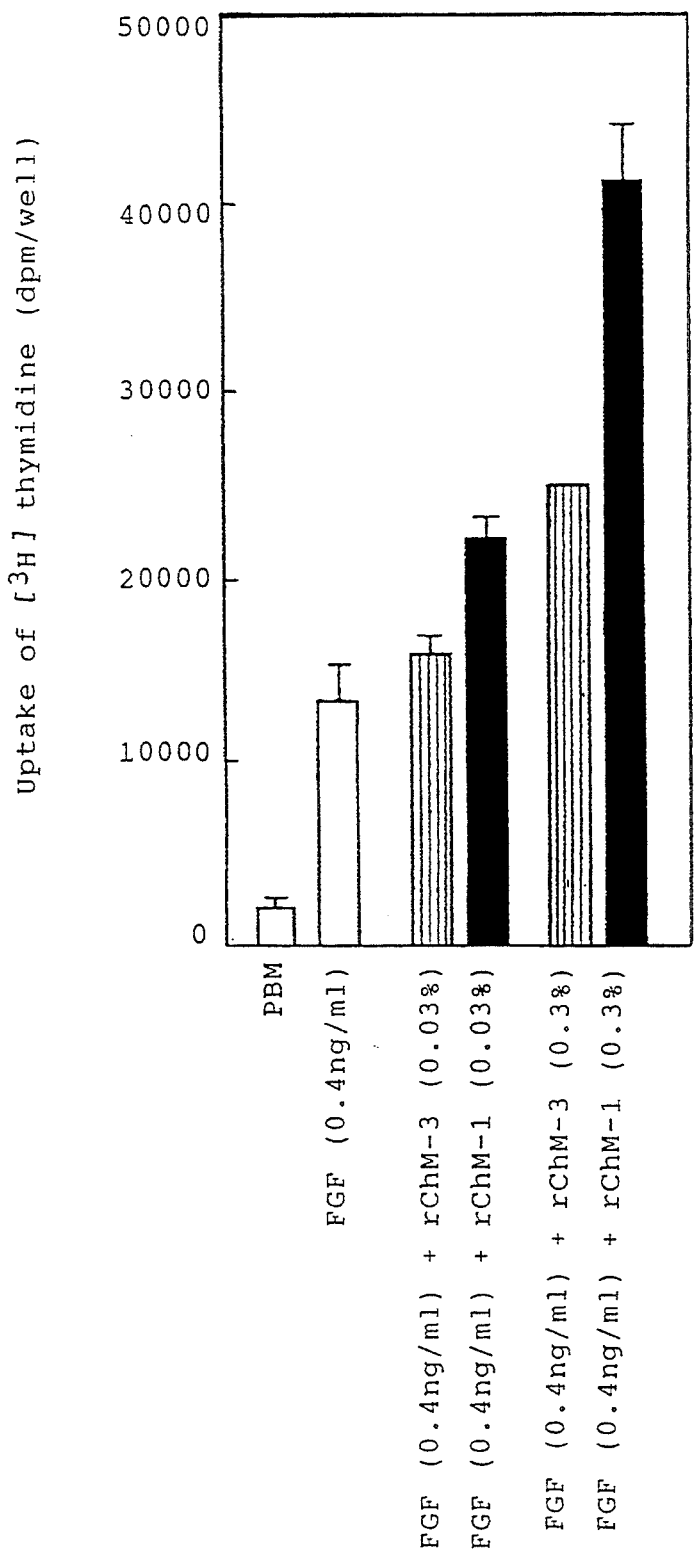
FIG. 5: Activity of recombinant chondromodulin-I protein present in the supernatant of cultured broth of transformed COS cells.

Evaluation of activities of recombinant chondromodulin-I protein obtained in Example 8 was carried out substantially in accordance with the description in Example 2. Results are given in FIG. 5 wherein YChM-1 and YChM-3 represents supernatant of cultured broth of COS cells transformed with expression plasmid pKCRCHM1 and pKCRCHM3, respectively. FIG. 5 shows that the uptake of radioactive thymidine was apparently increased in the presence of 0.3% (about 100 μl of supernatant) of recombinant-I chondromodulin protein, and it was about 20 folds of that observed in the absence of FGF and about 3.0 folds of that observed in the presence of 0.4 ng of FGF, demonstrating that the recombinant chondromodulin-I protein of the invention has a potential stimulating effect on the growth of chondrocytes.

What we claim is:

1. A purified and isolated protein which consists of the amino acid sequence shown in FIG. 6, wherein AAA is Met or Val, BBB is Glu or Thr, CCC is Gln or deletion, and DDD is Cys or Val, and which has an activity which (A) stimulates the growth of chondrocytes in the presence or absence of fibroblast growth factor, (B) inhibits the growth of tumors, or (C) is a combination of these activities.

2. A novel chondromodulin-I protein which is purified and isolated from cartilage of fetal bovine, which has a molecular weight of about 26,000 daltons on SDS-polyacrylamide gel electrophoresis, which stimulates the growth of chondrocytes in the presence or absence of fibroblast growth factor, and which consists of the amino acid sequence shown in FIG. 6, wherein AAA is Val, BBB is Thr, CCC is Gln and DDD is Cys.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
       ( A ) LENGTH: 121 amino acids
       ( B ) TYPE: amino acid
       ( C ) STRANDEDNESS: single
       ( D ) TOPOLOGY: linear ( i i ) MOLECULE TYPE: protein ( i i i ) HYPOTHETICAL:

( i v ) ANTI-SENSE:

( v ) FRAGMENT TYPE:

( v i ) ORIGINAL SOURCE:
       ( A ) ORGANISM: bovine
       ( B ) STRAIN:
       ( C ) INDIVIDUAL ISOLATE:
       ( D ) DEVELOPMENTAL STAGE:
       ( E ) HAPLOTYPE:
       ( F ) TISSUE TYPE: fetal cartilage
       ( G ) CELL TYPE:
       ( H ) CELL LINE:
       ( I ) ORGANELLE:

( v i i ) IMMEDIATE SOURCE:
       ( A ) LIBRARY:
       ( B ) CLONE:

( v i i i ) POSITION IN GENOME:
       ( A ) CHROMOSOME/SEGMENT:
       ( B ) MAP POSITION:
       ( C ) UNITS:

( i x ) FEATURE:
       ( A ) NAME/KEY: modified site
       ( B ) LOCATION: 7
       ( C ) IDENTIFICATION METHOD:
       ( D ) OTHER INFORMATION: /note="Xaa is Met or Val"

( i x ) FEATURE:
       ( A ) NAME/KEY: modified site
       ( B ) LOCATION: 10
       ( C ) IDENTIFICATION METHOD:
       ( D ) OTHER INFORMATION: /note="Xaa is Glu or Thr"

( i x ) FEATURE:
       ( A ) NAME/KEY: modified site
       ( B ) LOCATION: 84
       ( C ) IDENTIFICATION METHOD:
       ( D ) OTHER INFORMATION: /note="Xaa is Cys or Val"

( x ) PUBLICATION INFORMATION:
       ( A ) AUTHORS:
       ( B ) TITLE:
       ( C ) JOURNAL:
       ( D ) VOLUME:
       ( E ) ISSUE:
       ( F ) PAGES:
       ( G ) DATE:

(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:1:

```
Glu  Leu  Val  Arg  Lys  Ile  Xaa  Thr  Thr  Xaa  Thr  Thr  Arg  Arg  Leu
 1              5                        10                         15

Arg  Ser  Gly  Pro  Gln  Gly  Thr  Pro  Ala  Pro  Gly  Arg  Pro  Asn  Asn
                20                       25                         30

Gly  Thr  Arg  Pro  Ser  Val  Gln  Glu  Asp  Ala  Glu  Pro  Phe  Asn  Pro
                    35                       40                         45

Asp  Asn  Pro  Tyr  His  Gln  Gln  Glu  Gly  Glu  Ser  Met  Thr  Phe  Asp
                    50                       55                         60

Pro  Arg  Leu  Asp  His  Glu  Gly  Ile  Cys  Cys  Ile  Glu  Cys  Arg  Arg
                    65                       70                         75

Ser  Tyr  Thr  His  Cys  Gln  Lys  Ile  Xaa  Glu  Pro  Leu  Gly  Gly  Tyr
                    80                       85                         90

His  Pro  Trp  Pro  Tyr  Asn  Tyr  Gln  Gly  Cys  Arg  Ser  Ala  Cys  Arg
                    95                      100                        105

Val  Ile  Met  Pro  Cys  Ser  Trp  Trp  Val  Ala  Arg  Ile  Leu  Gly  Met
                   110                      115                        120

Val
```

(2) INFORMATION FOR SEQ ID NO:2:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (iii) HYPOTHETICAL:

(iv) ANTI-SENSE:

(v) FRAGMENT TYPE:

(vi) ORIGINAL SOURCE:
        (A) ORGANISM: bovine
        (B) STRAIN:
        (C) INDIVIDUAL ISOLATE:
        (D) DEVELOPMENTAL STAGE:
        (E) HAPLOTYPE:
        (F) TISSUE TYPE: fetal cartilage
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY: modified site
        (B) LOCATION: 7
        (C) IDENTIFICATION METHOD:
        (D) OTHER INFORMATION: /note="Xaa is Met or Val"

(ix) FEATURE:
        (A) NAME/KEY: modified site
        (B) LOCATION: 10
        (C) IDENTIFICATION METHOD:
        (D) OTHER INFORMATION: /note="Xaa is Glu or Thr"

(ix) FEATURE:
    (A) NAME/KEY: modified site
    (B) LOCATION: 83
    (C) IDENTIFICATION METHOD:
    (D) OTHER INFORMATION: /note="Xaa is Cys or Val"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:2:

```
Glu Leu Val Arg Lys Ile Xaa Thr Thr Xaa Thr Thr Arg Arg Leu
 1               5                  10                 15

Arg Ser Gly Pro Gln Gly Thr Pro Ala Pro Gly Arg Pro Asn Asn
                20                  25                 30

Gly Thr Arg Pro Ser Val Gln Glu Asp Ala Glu Pro Phe Asn Pro
                35                  40                 45

Asp Asn Pro Tyr His Gln Glu Gly Glu Ser Met Thr Phe Asp Pro
                50                  55                 60

Arg Leu Asp His Glu Gly Ile Cys Cys Ile Glu Cys Arg Arg Ser
                65                  70                 75

Tyr Thr His Cys Gln Lys Ile Xaa Glu Pro Leu Gly Gly Tyr His
                80                  85                 90

Pro Trp Pro Tyr Asn Tyr Gln Gly Cys Arg Ser Ala Cys Arg Val
                95                 100                105

Ile Met Pro Cys Ser Trp Trp Val Ala Arg Ile Leu Gly Met Val
               110                 115                120
```

(2) INFORMATION FOR SEQ ID NO:3:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: cDNA (iii) HYPOTHETICAL:

(iv) ANTI-SENSE:

(v) FRAGMENT TYPE:

(vi) ORIGINAL SOURCE:
        (A) ORGANISM: bovine
        (B) STRAIN:
        (C) INDIVIDUAL ISOLATE:
        (D) DEVELOPMENTAL STAGE:
        (E) HAPLOTYPE:
        (F) TISSUE TYPE: fetal cartilage
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
  (A) NAME/KEY: modified site
  (B) LOCATION: 252
  (C) IDENTIFICATION METHOD:
  (D) OTHER INFORMATION: /note="N is T, G, A or C"

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO:

(xi) SEQUENCE DESCRIPTION: SEQ ID NO:3:

```
GAACTGGTAA GAAAAATCRT GACCACARMG ACCACAAGAA GACTACGCAG CGGCCCTCAG     60
GGCACCCCAG CCCCTGGAAG ACCAAACAAC GGAACCAGAC CCAGCGTCCA AGAGGACGCA    120
GAGCCCTTCA ACCCAGACAA CCCTTACCAC CAGNNNGAAG GAGAAAGCAT GACATTCGAC    180
CCCAGACTGG ATCATGAAGG AATCTGCTGT ATAGAATGCA GGAGGAGCTA CACCCACTGC    240
CAGAAGATCK KNGAGCCTCT GGGGGGCTAC CACCCATGGC CCTATAACTA CCAGGGCTGC    300
CGTTCCGCCT GCAGAGTCAT CATGCCCTGT AGCTGGTGGG TGGCCCGCAT CCTGGGCATG    360
GTGTGA                                                              366
```

(2) INFORMATION FOR SEQ ID NO:4:

(i) SEQUENCE CHARACTERISTICS:
    (A) LENGTH: 365 base pairs
    (B) TYPE: nucleic acid
    (C) STRANDEDNESS: single
    (D) TOPOLOGY: linear (ii) MOLECULE TYPE: cDNA (iii) HYPOTHETICAL:

(iv) ANTI-SENSE:

(v) FRAGMENT TYPE:

(vi) ORIGINAL SOURCE:
    (A) ORGANISM: bovine
    (B) STRAIN:
    (C) INDIVIDUAL ISOLATE:
    (D) DEVELOPMENTAL STAGE:
    (E) HAPLOTYPE:
    (F) TISSUE TYPE: fetal cartilage
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY: modified site
    (B) LOCATION: 251
    (C) IDENTIFICATION METHOD:
    (D) OTHER INFORMATION: /note="N is T, G, A or C"

(x) PUBLICATION INFORMATION:
    (A) AUTHORS:
    (B) TITLE:
    (C) JOURNAL:

(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:4:

```
GAACTGGTAA GAAAAATCRT GACCACARMG ACCACAAGAA GACTACGCAG CGGCCCTCAG    60
GGCACCCCAG CCCCTGGAAG ACCAAACAAC GGAACCAGAC CCAGCGTCCA AGAGGACGCA   120
GAGCCCTTCA ACCCAGACAA CCCTTACCAC CAGNNGAAGG AGAAAGCATG ACATTCGACC   180
CCAGACTGGA TCATGAAGGA ATCTGCTGTA TAGAATGCAG GAGGAGCTAC ACCCACTGCC   240
AGAAGATCKK NGAGCCTCTG GGGGGCTACC ACCCATGGCC CTATAACTAC CAGGGCTGCC   300
GTTCCGCCTG CAGAGTCATC ATGCCCTGTA GCTGGTGGGT GGCCCGCATC CTGGGCATGG   360
TGTGA                                                                365
```

(2) INFORMATION FOR SEQ ID NO:5:

(i) SEQUENCE CHARACTERISTICS:
(A) LENGTH: 364 base pairs
(B) TYPE: nucleic acid
(C) STRANDEDNESS: single
(D) TOPOLOGY: linear (ii) MOLECULE TYPE: cDNA (iii) HYPOTHETICAL:

(iv) ANTI-SENSE:

(v) FRAGMENT TYPE:

(vi) ORIGINAL SOURCE:
(A) ORGANISM: bovine
(B) STRAIN:
(C) INDIVIDUAL ISOLATE:
(D) DEVELOPMENTAL STAGE:
(E) HAPLOTYPE:
(F) TISSUE TYPE: fetal cartilage
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY: modified site
(B) LOCATION: 250
(C) IDENTIFICATION METHOD:
(D) OTHER INFORMATION: /note="N is T, G, A or C"

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:5:

| | | | | | |
|---|---|---|---|---|---|
| GAACTGGTAA | GAAAAATCRT | GACCACARMG | ACCACAAGAA | GACTACGCAG | CGGCCCTCAG | 60
| GGCACCCCAG | CCCCTGGAAG | ACCAAACAAC | GGAACCAGAC | CCAGCGTCCA | AGAGGACGCA | 120
| GAGCCCTTCA | ACCCAGACAA | CCCTTACCAC | CAGNGAAGGA | GAAAGCATGA | CATTCGACCC | 180
| CAGACTGGAT | CATGAAGGAA | TCTGCTGTAT | AGAATGCAGG | AGGAGCTACA | CCCACTGCCA | 240
| GAAGATCKKN | GAGCCTCTGG | GGGGCTACCA | CCCATGGCCC | TATAACTACC | AGGGCTGCCG | 300
| TTCCGCCTGC | AGAGTCATCA | TGCCCTGTAG | CTGGTGGGTG | GCCCGCATCC | TGGGCATGGT | 360
| GTGA | | | | | | 364

( 2 ) INFORMATION FOR SEQ ID NO:6:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL:

( i v ) ANTI-SENSE:

( v ) FRAGMENT TYPE:

( v i ) ORIGINAL SOURCE:
        ( A ) ORGANISM: bovine
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE: fetal cartilage
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: modified site
        ( B ) LOCATION: 249
        ( C ) IDENTIFICATION METHOD:
        ( D ) OTHER INFORMATION: /note="N is T, G, A or C"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:6:

| | | | | | |
|---|---|---|---|---|---|
| GAACTGGTAA | GAAAAATCRT | GACCACARMG | ACCACAAGAA | GACTACGCAG | CGGCCCTCAG | 60
| GGCACCCCAG | CCCCTGGAAG | ACCAAACAAC | GGAACCAGAC | CCAGCGTCCA | AGAGGACGCA | 120
| GAGCCCTTCA | ACCCAGACAA | CCCTTACCAC | CAGGAAGGAG | AAAGCATGAC | ATTCGACCCC | 180
| AGACTGGATC | ATGAAGGAAT | CTGCTGTATA | GAATGCAGGA | GGAGCTACAC | CCACTGCCAG | 240
| AAGATCKKNG | AGCCTCTGGG | GGGCTACCAC | CCATGGCCCT | ATAACTACCA | GGGCTGCCGT | 300

TCCGCCTGCA GAGTCATCAT GCCCTGTAGC TGGTGGGTGG CCCGCATCCT GGGCATGGTG    360

TGA    363

(2) INFORMATION FOR SEQ ID NO:7:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (ii) MOLECULE TYPE: cDNA (iii) HYPOTHETICAL:

(iv) ANTI-SENSE:

(v) FRAGMENT TYPE:

(vi) ORIGINAL SOURCE:
        (A) ORGANISM: bovine
        (B) STRAIN:
        (C) INDIVIDUAL ISOLATE:
        (D) DEVELOPMENTAL STAGE:
        (E) HAPLOTYPE:
        (F) TISSUE TYPE: fetal cartilage
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:7:

GAGTTGGTCA GGAAGATAAT GACCACAGAG ACCACAAGAA GACTACGCAG CGGCCCTCAG    60

GGCACCCCAG CCCCTGGAAG ACCAAACAAC GGAACCAGAC CCAGCGTCCA AGAGGACGCA    120

GAGCCCTTCA ACCCAGACAA CCCTTACCAT CAGGAAGGAG AAAGCATGAC ATTCGACCCC    180

AGACTGGATC ATGAAGGCAT CTGCTGTATA GAATGCAGGA GGAGCTACAC CCACTGCCAG    240

AAGATCTGTG AGCCTCTGGG GGGCTACCAC CCATGGCCCT ATAACTACCA    290

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE:

(i i i) HYPOTHETICAL:

(i v) ANTI-SENSE:

(v) FRAGMENT TYPE:

(v i) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(v i i) IMMEDIATE SOURCE:
    (A) LIBRARY:
    (B) CLONE:

(v i i i) POSITION IN GENOME:
    (A) CHROMOSOME/SEGMENT:
    (B) MAP POSITION:
    (C) UNITS:

(i x) FEATURE:
    (A) NAME/KEY: modified site
    (B) LOCATION: 9
    (C) IDENTIFICATION METHOD:
    (D) OTHER INFORMATION: /note="N is T, G, C or A"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(x i) SEQUENCE DESCRIPTION: SEQ ID NO:8:

GARTTRGTNA GRAARATHRT    20

(2) INFORMATION FOR SEQ ID NO:9:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE:

(i i i) HYPOTHETICAL:

(i v) ANTI-SENSE:

(v) FRAGMENT TYPE:

(v i) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(v i i) IMMEDIATE SOURCE:
    (A) LIBRARY:
    (B) CLONE:

(v i i i) POSITION IN GENOME:
    (A) CHROMOSOME/SEGMENT:
    (B) MAP POSITION:
    (C) UNITS:

(i x) FEATURE:
    (A) NAME/KEY: modified site
    (B) LOCATION: 6
    (C) IDENTIFICATION METHOD:
    (D) OTHER INFORMATION: /note="N is T, G, C or A"

(i x) FEATURE:
    (A) NAME/KEY:
    (B) LOCATION: 9
    (C) IDENTIFICATION METHOD:
    (D) OTHER INFORMATION: /note="N is T, G, C or A"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(x i) SEQUENCE DESCRIPTION: SEQ ID NO:9:

GARCTNGTNA GRAARATHRT        20

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE:

(i i i) HYPOTHETICAL:

(i v) ANTI-SENSE:

(v) FRAGMENT TYPE:

(v i) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(v i i) IMMEDIATE SOURCE:
        (A) LIBRARY:
        (B) CLONE:

(v i i i) POSITION IN GENOME:
        (A) CHROMOSOME/SEGMENT:
        (B) MAP POSITION:
        (C) UNITS:

(i x) FEATURE:
        (A) NAME/KEY: modified site
        (B) LOCATION: 12
        (C) IDENTIFICATION METHOD:
        (D) OTHER INFORMATION: /note="N is T, G, C or A"

(x) PUBLICATION INFORMATION:
        (A) AUTHORS:
        (B) TITLE:
        (C) JOURNAL:

( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:10:

TGRTARTTRT ANGGCCA                17

( 2 ) INFORMATION FOR SEQ ID NO:11:

( i ) SEQUENCE CHARACTERISTICS:
      ( A ) LENGTH: 28 amino acids
      ( B ) TYPE: amino acid
      ( C ) STRANDEDNESS: single
      ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
      ( A ) ORGANISM:
      ( B ) STRAIN:
      ( C ) INDIVIDUAL ISOLATE:
      ( D ) DEVELOPMENTAL STAGE:
      ( E ) HAPLOTYPE:
      ( F ) TISSUE TYPE:
      ( G ) CELL TYPE:
      ( H ) CELL LINE:
      ( I ) ORGANELLE:

( v i i ) IMMEDIATE SOURCE:
      ( A ) LIBRARY:
      ( B ) CLONE:

( v i i i ) POSITION IN GENOME:
      ( A ) CHROMOSOME/SEGMENT:
      ( B ) MAP POSITION:
      ( C ) UNITS:

( i x ) FEATURE:
      ( A ) NAME/KEY: modified site
      ( B ) LOCATION: 7
      ( C ) IDENTIFICATION METHOD:
      ( D ) OTHER INFORMATION: /note="Xaa is Val or Met"

( i x ) FEATURE:
      ( A ) NAME/KEY: modified site
      ( B ) LOCATION: 9
      ( C ) IDENTIFICATION METHOD:
      ( D ) OTHER INFORMATION: /note="Xaa is unknown"

( x ) PUBLICATION INFORMATION:
      ( A ) AUTHORS:
      ( B ) TITLE:
      ( C ) JOURNAL:
      ( D ) VOLUME:
      ( E ) ISSUE:
      ( F ) PAGES:
      ( G ) DATE:
      ( H ) DOCUMENT NUMBER:
      ( I ) FILING DATE:
      ( J ) PUBLICATION DATE:
      ( K ) RELEVANT RESIDUES IN SEQ ID NO:

( x i ) SEQUENCE DESCRIPTION: SEQ ID NO:11:

Glu Leu Val Arg Lys Ile Xaa Thr Xaa Glu Thr Thr Arg Arg Leu
 1               5                  10                    15

Arg Ser Gly Pro Gln Gly Gly Pro Ala Pro Gly Arg Pro
                20                  25

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:12:

Ile Val Glu Pro Leu Gly Gly Tyr Asp Pro Trp Pro Tyr Asn Tyr
1               5                   10                  15

Gln Gly Ser Arg Ser Ala
            20